United States Patent
Astier et al.

(10) Patent No.: US 9,012,329 B2
(45) Date of Patent: Apr. 21, 2015

(54) NANOGAP IN-BETWEEN NOBLE METALS

(71) Applicant: International Business Machines Corporation, Armonk, NY (US)

(72) Inventors: Yann Astier, White Plains, NY (US); Jingwei Bai, Elmsford, NY (US); Michael F. Lofaro, Danbury, CT (US); Satyavolu S. Papa Rao, Poughkeepsie, NY (US); Joshua T. Smith, Croton on Hudson, NY (US); Chao Wang, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 48 days.

(21) Appl. No.: 13/856,471

(22) Filed: Apr. 4, 2013

(65) Prior Publication Data

US 2014/0302675 A1    Oct. 9, 2014

(51) Int. Cl.
*H01L 21/311* (2006.01)
*H01L 21/306* (2006.01)

(52) U.S. Cl.
CPC ................................. *H01L 21/30625* (2013.01)

(58) Field of Classification Search
CPC ...................... H01L 21/7682; H01L 21/76852; H01L 21/3142
USPC ......... 438/619, 622, 626, 627, 691, 692, 720, 438/742, 696, 697, 701; 216/100, 101, 102
See application file for complete search history.

(56) References Cited

U.S. PATENT DOCUMENTS

| | | | |
|---|---|---|---|
| 6,849,911 B2* | 2/2005 | Monty et al. | 257/414 |
| 7,256,107 B2 | 8/2007 | Takeuchi | |
| 7,385,295 B2* | 6/2008 | Son et al. | 257/776 |
| 7,537,883 B2 | 5/2009 | Yu | |
| 8,329,559 B2 | 12/2012 | Takeuchi | |
| 2002/0168810 A1* | 11/2002 | Jackson | 438/172 |
| 2004/0201929 A1* | 10/2004 | Hashimoto et al. | 360/324.1 |
| 2011/0268884 A1* | 11/2011 | Wind et al. | 427/272 |

FOREIGN PATENT DOCUMENTS

| | | |
|---|---|---|
| KR | 1020060081858 | 7/2006 |
| KR | 1020100091751 | 8/2010 |

OTHER PUBLICATIONS

Y-K. Choi et al. "Sublithographic nanofabrication technology for nanocatalysts and DNA chips" J. Vac. Sci. Technol. B 21(6), 2951 (2003).

* cited by examiner

*Primary Examiner* — Lan Vinh
(74) *Attorney, Agent, or Firm* — Louis J. Percello; Otterstedt, Ellenbogen & Kammer, LLP

(57) ABSTRACT

A nanogap of controlled width in-between noble metals is produced using sidewall techniques and chemical-mechanical-polishing. Electrical connections are provided to enable current measurements across the nanogap for analytical purposes. The nanogap in-between noble metals may also be formed inside a Damascene trench. The nanogap in-between noble metals may also be inserted into a crossed slit nanopore framework. A noble metal layer on the side of the nanogap may have sub-layers serving the purpose of multiple simultaneous electrical measurements.

20 Claims, 6 Drawing Sheets

NANOGAP IN-BETWEEN NOBLE METALS

BACKGROUND

The present invention relates to nano-structures capable of molecular scale operations. In particular it relates to structures containing small nanogaps, or slits, that are in-between noble metal layers.

BRIEF SUMMARY

A nanogap of controlled width in-between noble metals is produced using sidewall techniques and chemical-mechanical-polishing. Electrical connections are provided to enable current measurements across the nanogap for analytical purposes. The nanogap in-between noble metals may also be formed inside a Damascene trench. The nanogap in-between noble metals may also be inserted into a crossed slit nanopore framework. A noble metal layer on the side of the nanogap may have sub-layers serving the purpose of multiple simultaneous electrical measurements.

BRIEF DESCRIPTION OF THE SEVERAL VIEWS OF THE DRAWINGS

These and other features of the present invention will become apparent from the accompanying detailed description and drawings, wherein.

DETAILED DESCRIPTION

Figure 1A:
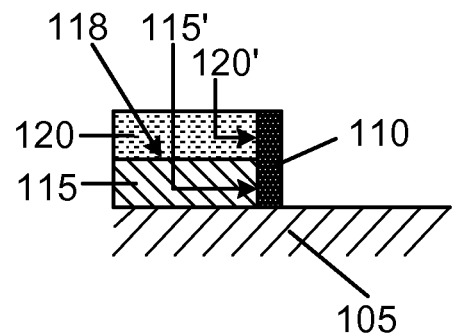
FIGS. 1A-1F show schematic cross sectional views of fabricating a nanogap in-between noble metals, according to an embodiment of the disclosure.

Small slits, often referred to as nanogaps, find applications in a wide variety of endeavors in the fields of physics, biology, chemistry, and others. For example, nanogaps may find uses for DNA sequencing. Techniques for rapid sequencing successive nucleotide bases in a strand of DNA are useful in basic biological research, as well as, in numerous applied fields such as diagnostics, biotechnology, and forensic biology. A nanogap based device may provide solution for rapid sequencing of DNA single molecules by detecting electrical signals as the DNA passes through the nanogap. In general, molecules in solution may electrophoretically be driven through a nanogap or nanopore. Such process may ensure that the native order of the nucleo-bases are reflected in the sequence of any signal detected across the nanogap as the DNA passes through it.

In order to distinguish individual molecules, or individual nucleo-bases in a DNA sequence, the width of the nanogap should be shrunk down to the sub-10 nm region, with a 0.5 nm to 5 nm range being possibly of most interest.

For detecting what molecular structure traverses the nanogap, electrical means, such as tunneling current across the nanogap may be useful. In this regard noble metals show advantages since they are good conductors and chemically inert. The latter being useful in order not to chemically alter either the solution passing through the nanogap in-between the noble metals, or the electrodes themselves. For example, it would be advantageous to create few nanometer wide Pd nanogap for the purpose of DNA sequencing. One may detect variations in a tunneling current across the noble metal nanogap which in effect may act as a Pd/DNA base/Pd tunneling junction.

Embodiments of the present invention teach nanogaps in-between noble metals, produced rapidly, and reproducibly. The width of such nanogaps can be in the range of interest for tunneling current measurements in the gaps. The fabrication of these in-between noble metal nanogaps may rely on techniques found in microelectronics processing. The process for reproducible production of nanogaps with controlled sizes down to the nm regime would be useful for many applications.

The general approach of fabricating a nanogap in the embodiments of the present invention uses sidewall techniques and chemical-mechanical-polishing (CMP) techniques. These procedures are known in the arts, in particular in the semiconductor manufacturing arts; hence, only briefly, and only in regard to their salient features are these procedures discussed herein.

A sidewall technique, also referred to as sidewall image transfer, which typically is capable of producing features smaller than it is possible with lithography that is contemporarily extant, is based on a conformal deposition of a film (or layer) over a step (or ledge, or sidewall), which deposition is then followed by a directional, typically vertical, etching of the film. The result is a thin layer, or sidewall, on the side of the step. The thickness, or width, of this sidewall is not determined by lithography, but by the interplay of the deposited film thickness, the height of the step, the conformality of the deposition, and the degree of directionality of the etch. In general, the thickness of the sidewall can be very well, and reproducibly, controlled. Such sidewalls may be produced to thicknesses down to around 0.5 nm and up to hundreds of nm-s.

CMP, chemical-mechanical-polishing (sometimes also referred to as chemical-mechanical-planarization), as its name implies, is a technique for thinning down and planarize films, (or layers) present on a surface. CMP is widely used in semiconductor manufacturing for a number of various materials. However, because CMP is at times cumbersome to apply to noble metals, an embodiment of the present disclosure teaches a noble metal nanogap, or expressed differently a nanogap in-between noble metals, without the need to directly CMP a noble metal.

FIGS. 1A-1F show schematic cross sectional views of fabricating a nanogap in-between noble metals, according to an embodiment of the disclosure. In this embodiment of the disclosure noble metals when in need of removal are typically etched away, without the use of CMP.

FIG. 1A shows an initial stage in producing a nanogap. A first layer 115 has been disposed, or deposited, over a substrate 105. The first layer 115 comprises a first noble metal, typically the first layer 115 is composed of one or more noble metals. As it is known, such noble metals may be selected from amongst the following elements: Ru, Rh, Pd, Ag, Os, Ir, Pt, Au, and alloys composed of these materials. In a representative embodiment the first noble metal of the first layer 115 may be Pd (palladium).

Still referring to FIG. 1A, a first adjunct layer 120 is disposed over the first layer 115. The first layer 115 and the first adjunct layer 120 are in direct physical contact and have a common interface 118. The first adjunct layer 120 may be composed of a wide variety of material. The requirements for the first adjunct layer 120 are functional in nature: it has to be polishable in a CMP process, and when at a later stage a noble metal is etched, the first adjunct layer 120 has to withstand such an etch. By way of example, without intent of limitation, the first adjunct layer 120 may be chosen to be a hardmask layer. Hardmasks are known in the art, for example, they may be a dielectric, such as an oxide, or a nitride, or a metal, such as TiN, W, or Ta, and others.

The first layer 115 and the first adjunct layer 120 have been deposited over a substrate 105. The substrate 105 may be of any kind of material, conductor, insulator, semiconductor, crystalline, or not crystalline. The specific needs of any given fabrication may determine the nature of the substrate 105. For sake of an example, the substrate 105 may be a Si wafer. The deposition of the first layer 115 and the first adjunct 120 layer typically follows known methods of the arts, for instance, but not limited to evaporation, sputtering, atomic layer deposition (ALD), epitaxy, and others.

Still referring to FIG. 1A, the first layer 115 and the first adjunct layer 120 have been patterned, by known methods in the art, for instance, but not limited to lift-off or RIE etch processes, in a manner to have their respective sidewalls 115', 120' exposed. A sacrificial layer 110 of a controlled thickness has been formed on the exposed sidewalls 115', 120', using a sidewall technique. The sacrificial layer 110 is substantially perpendicular to the common interface 118 of first layer 115 and the first adjunct layer 120. The sacrificial layer 110 may be ALD grown $Al_2O_3$, which may be controlled to subnanometer thickness. Other materials, such as, without limitation Al, Cr, $SiO_2$, or other deposition methods may also be used. Generally, preference would be given to uniform conformal coating of the sidewalls 115', 120', and the possibility to selectively remove (at a later stage) the sacrificial layer 110, leaving noble metal comprising layers intact.

Figure 1B:
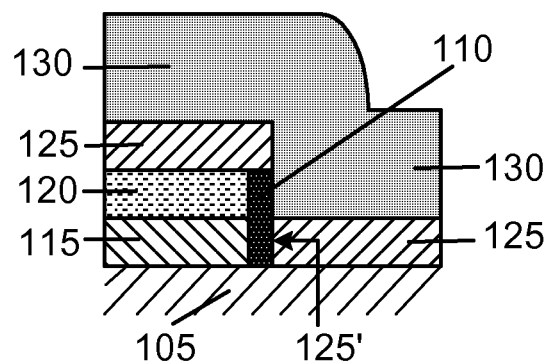

FIG. 1B shows a subsequent stage in producing a nanogap in-between noble metals. A second layer 125 covering the first adjunct layer 120, followed by a second adjunct layer 130 covering the second layer 125, have been disposed. These dispositions have also been performed by methods known in the art. As far as the physical region of interest for the discussed processing, typically the regions displayed on the figures, the second layer 125 and the second adjunct layer 130 have been blanket disposed; meaning without masking.

The choices for the material composition of the second layer 125 are the same as those of the first layer 115. The second layer 125 comprises a second noble metal, and typically it is composed of one or more noble metals. In a representative embodiment the second noble metal of the second layer 125 may also be Pd. The second layer 125 may be deposited somewhat directionally, as shown in FIG. 1B, but a conformal disposition would cause no problems. Small amounts of materials on sidewalls may always be removed by CMP. The thickness of the second layer 125 is typically chosen to be close to that of the first layer 115, but some applications may have preference having the first 115 and second 125 layers of differing thickness.

The second adjunct layer 130 is very similar to the first adjunct layer 120. The second adjunct layer 130 may be composed of a wide variety of materials. The requirements for the second adjunct layer 130 are functional in nature: it has to be polishable in a CMP process, and when at a later stage a noble metal is etched, the second adjunct layer 130 has to withstand such an etch. By way of example, without intent of limitation, second adjunct layer 130 may be chosen to be a hardmask layer. Hardmasks are known in the art, for example, they may be a dielectric, such as an oxide, or a nitride, or a metal, such as TiN, W, or Ta, and others. The second adjunct layer 130 may typically be deposited conformally, as shown in FIG. 1B.

Still referring to FIG. 1B, due to the order and the manner of their dispositions, or depositions, the sacrificial layer 110 separates a sidewall 115' of the first layer 115 from a sidewall 125' of the second layer 125, as is evident in FIG. 1B.

Figure 1C:
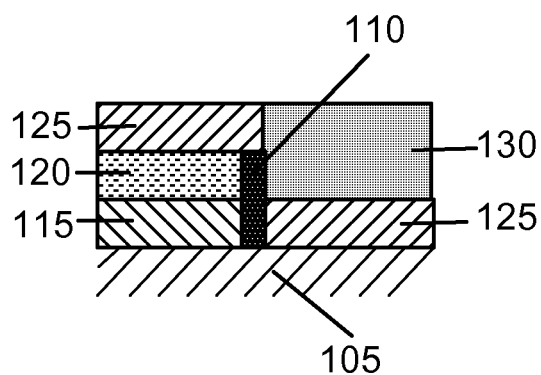
Figure 1D:
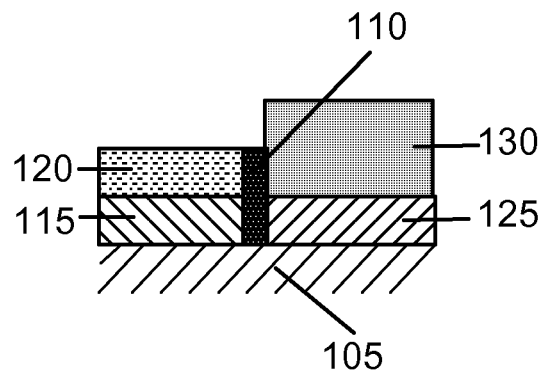

FIG. 1C shows a subsequent stage in producing a nanogap in-between noble metals. The second adjunct layer 130 went through a CMP process until the second layer 125 has an exposed portion over the first adjunct layer 120, and consequently over the first layer 115. At this stage the portion of the second layer 125 that is over the first adjunct layer 120 is exposed to an etch. This etch removes the noble metal comprising materials but it is sufficiently selective relative to the adjunct layers. For instance, if the noble metal is Pd, such etch, by way of example, may be Ar (argon) sputtering. During this etch the rest of the second layer 125 is protected by the part of the second adjunct layer 130 which remained in place after the CMP process. FIG. 1D shows the stage where the exposed portion of the second layer 125 has been selectively etched away.

Figure 1E:
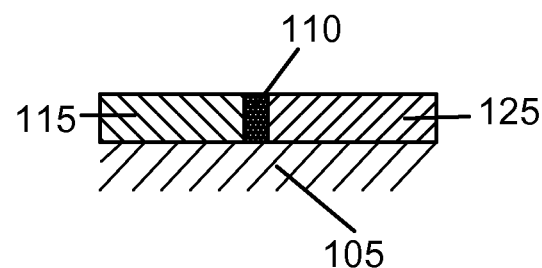

FIG. 1E shows a subsequent stage in producing a nanogap in-between noble metals. The first adjunct layer 120 and the second adjunct layer 130 have been polished until either of the first layer 115 or the second layer 125 become exposed. Or, if they are essentially of the same thickness, which may be a typical case, and which is displayed in the figures, they become exposed roughly simultaneously. Naturally, during this CMP process the thin sacrificial layer 110 is also polished down to the level of the noble metal first 115 or second 125 layer.

Figure 1F:
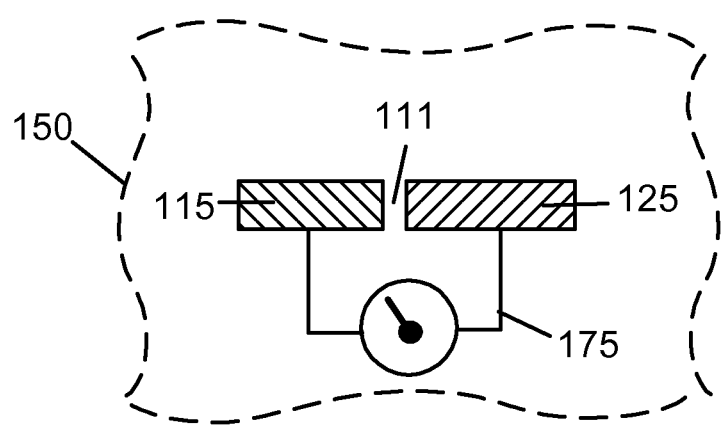

FIG. 1F shows what is essentially the final stage in producing a nanogap in-between noble metals. The sacrificial layer 110 has been etched away by known methods in the art, and in its place a nanogap 111 has appeared in-between the noble metal comprising layers 115, 125. The substrate 105 has also been removed by known methods in the art. Through the opened nanogap 111 two potential reservoirs on opposing sides of the layers 115, 125 will be in fluid connectivity, meaning molecules that would fit through the nanogap 111 would be able to pass. The selected width of the nanogap 111 essentially equals the original controlled thickness of the sacrificial layer 110, hence the capability of reproducibly and precisely create nanogaps by the embodiments of the invention.

Still referring to FIG. 1F, the noble metal comprising conducting first 115 and second 125 layers are provided with an electrical connection 175. Such connection then allows for a variety of electrical measurements, for example, current measurements across the nanogap, as symbolically indicated in FIG. 1F. Such an arrangement may be used then, for instance, for tunneling current measurements across the nanogap, as various molecules, or molecule parts are passing through the nanogap.

It is understood that the nanogap 111 and the noble metal layers are part of, and are supported by, some device structure 150, as symbolically indicated in FIG. 1F. There maybe several choices for such a device structure, with the obvious possibility of a silicon wafer that may surround the noble metal nanogap. However, the silicon wafer is mentioned only by way of example and no limitation should be understood; any and all device structures 150 would be within the scope of the embodiments of the present disclosure.

The first and second layers 115, 125, each may be of a single noble metal, or containing a combination of noble metals, or being an alloy containing only some percentage of a noble metal. Also, the first and second layers 115, 125, may have the same composition, or a differing composition, as applications would warrant it. In representative embodiment of the invention the first noble metal of the first layer 115 and the second noble metal of the second layer 125 are both Pd.

The selected width of the nanogap 111 may be anywhere about between 0.5 nm and 100 nm, but more typically about between 1.5 nm and 5 nm. As mentioned earlier the two noble metal comprising layers may be of a same thickness, but not necessarily so, depending on potential applications. Typical layer thicknesses may be in the same range as the width of the nanogap, anywhere between about 0.5 nm and 100 nm, but more typically about between 2 nm and 20 nm.

In an alternate embodiment of the invention one may use CMP for thinning and planarizing the noble metal layers themselves. FIGS. 2A-2D show schematic cross sectional views of fabricating a nanogap in-between noble metals, according to such an alternate embodiment of the disclosure. These figures also show a few of the details of the sidewall technique for forming the nanogap.

Figure 2A:
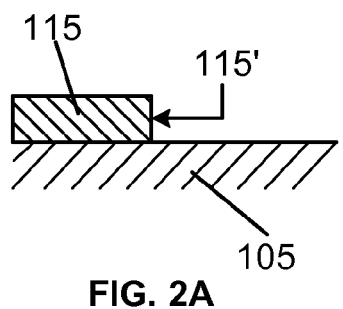
FIGS. 2A-2D show schematic cross sectional views of fabricating a nanogap in-between noble metals, according to an alternate embodiment of the disclosure.

FIG. 2A shows an initial stage in producing a nanogap in-between noble metals. A first layer 115 has been disposed over a substrate, and its sidewall 115' has been exposed. The first layer 115 of the embodiment discussed herein, which comprises a first noble metal, is essentially the same layer as the earlier introduced first layer 115 with reference to FIGS. 1A-1F. Hence its properties are listed here, they have already been given in the discussion referring to FIGS. 1A-1F. The same consideration is valid for all the elements depicted in FIGS. 2A-2D that carry the same indicator numbers as elements in FIGS. 1A-1F, such as the substrate 105, the second layer 125, and the sacrificial layer 110. They all have been presented earlier.

Figure 2C:
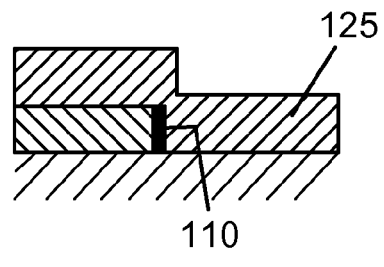
Figure 2B:
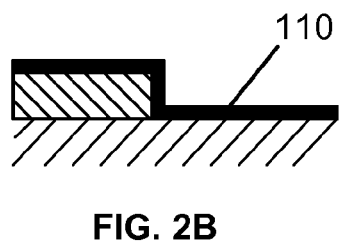

FIG. 2B shows a subsequent stage in producing a nanogap in-between noble metals. A sacrificial layer 110 of a controlled thickness is conformally disposed over the first layer 115 and its exposed sidewall 115'. FIG. 2C shows the state when in the framework of the sidewall technique the sacrificial layer 110 has been directionally etched and it is present only on the sidewall 115' of the first layer 115. A second layer 125 has been disposed over the first layer 115 and the sacrificial sidewall layer 110. The as deposited thickness of the second layer 125 may typically be chosen to be somewhat thicker than the first layer 115. This is the case displayed in FIG. 2C. In such as case, after a CMP process the first and second layers 115, 125 would end up being essentially of the same thickness. If the second layer 125 is chosen to be thinner than the first layer 115, one can end up with differing thicknesses for the noble metal layers 115, 125.

Figure 2D:
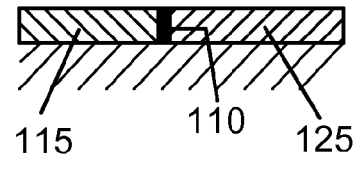

FIG. 2D shows a subsequent stage in producing a nanogap in-between noble metals. The second layer 125 has been thinned and planarized by a CMP process. In some embodiments one may continue with the CMP further to thin the first layer 115, as well. FIG. 2D is the same as FIG. 1E, since one has arrived to very the same stage of nanogap fabrication. Next, the sacrificial sidewall layer 110 and the substrate 105 are being removed, and electrical connections made, with the end result not shown here because it is the same as shown in FIG. 1F. All the considerations discussed in reference to FIG. 1E are applicable for this embodiment, as well.

In-between the states shown in FIGS. 2C and 2D the layers comprising noble metals have been subjected to a CMP step. Using standard CMP slurries this step may turn out to be unduly slow. The rate of noble metal CMP may be speeded up by using a slurry that contains an abrasive substance. By way of example, without limitation, such an abrasive substance may be W (tungsten) powder.

Figure 3A:
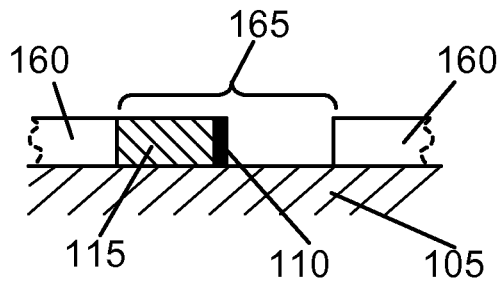
FIGS. 3A-3C show schematic cross sectional views of fabricating a nanogap in-between noble metals inside a Damascene trench.
Figure 3B:
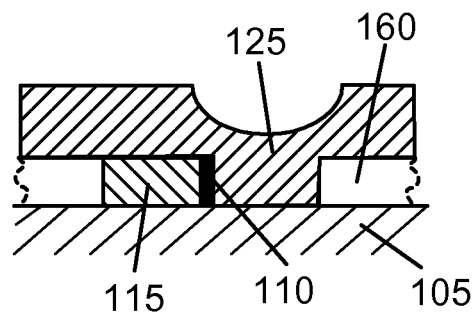
Figure 3C:
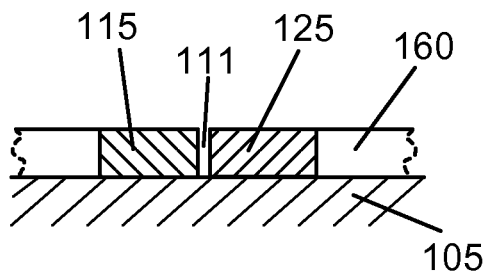

A further variation on an embodiment when CMP is used on noble metal containing layers is shown in FIGS. 3A-3C. The difference compared to the embodiment discussed with reference to FIGS. 2A-2D, is that now the nanogap in-between noble metals is fabricated inside a trench of a support layer. The large area of the support layer may facilitate the CMP process of the noble metal layers. The CMP can be done by landing on the support layer, and consequently having better film thickness control than with the blank noble metal polishing described above. Disposing metal layers inside prefabricated trenches, and then polish and planarize them is a known technique in the semiconductor processing art called Damascene. Accordingly, the embodiment shown in FIGS. 3A-3C may be referred to as fabricating a noble metal nanogap inside a Damascene trench.

As before, all the elements depicted in FIGS. 3A-3C that carry the same indicator numbers as elements in FIGS. 1A-1F are the same, and they characteristics need not be discussed again. FIG. 3A shows an initial stage in producing a nanogap in-between noble metals. There is a trench 165 in a support layer 160 over a substrate 105. The support layer 160 may be a dielectric or a metal, depending on the specifics of a planned application. For example, without limitation, the support layer may be an oxide, or a nitride, or metal such as TiN, W, or Ta, and others.

The trench 165 may have been fabricated with one of the many standard processes of the art for such purposes. The thickness of the support layer 160 is similar to the thickness expected from the noble metal layer of the nanogap structure to be fabricated. The trench 165 typically penetrates through the whole support layer 160, down to the substrate 105. The first layer 115 and the sacrificial layer 110 are formed inside the trench 165 of the support layer 160 by methods known in the art.

FIG. 3B shows that the second layer 125 has been blanket disposed over the first layer 115 and the support layer 160, therein filling the trench 165. Hence the surface of the second layer 125 is dipping over the trench. FIG. 3C shows the state after the second layer 125 has been polished. It may be advantageous to also thin down the support layer 160 and the first layer 115 in this CMP process. The sacrificial layer 110 has also been removed, and a nanogap 111 formed in its place. Following the removal of the substrate, at least locally, the nanogap containing structure of the presently discussed embodiment is the same as the one of FIG. 1F, with the possible exception that some of the support layer 160 may be left in place.

Figure 4A:
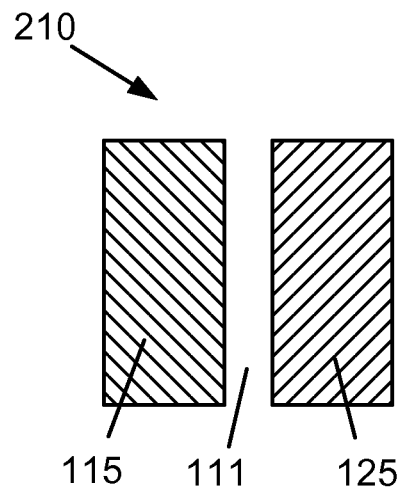
FIGS. 4A-4C show using a nanogap in-between noble metals in a nanopore framework, according to an embodiment of the disclosure.
Figure 4B:
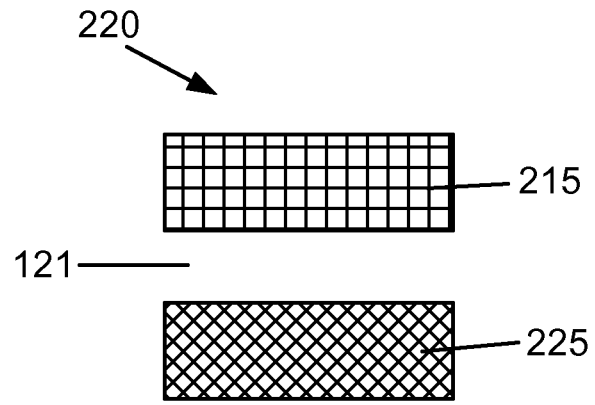
Figure 4C:
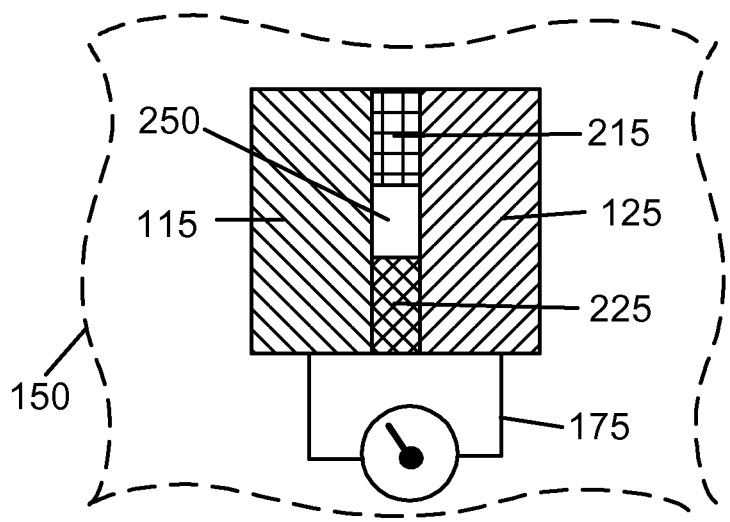

FIGS. 4A-4C show using a nanogap in-between noble metals in a nanopore framework, according to an embodiment of the disclosure. Nanopores and their fabrication with microelectronics techniques have already been disclosed by inventors in common with the instant application in the commonly owned U.S. patent application Ser. No. 13/536,915, filed Jun. 28, 2012, incorporated herein be reference. Accordingly, herein only the most salient features of the nanopore framework will be presented.

The earlier disclosed nanopores are fabricated by forming slits, or nanogaps, on two strata, (or layers), and crossing the nanogaps to create a nanopore at their intersection. The embodiment of the instant disclosure presented on FIGS. 4A-4C uses the nanogap in-between two noble metal layers as one of the two strata of the nanopore, while the other stratum of the nanopore is restricted to insulating materials. Consequently, electrical measurements can be made across the nanogap while the substances passing through the nanogap are restricted in size by the nanopore.

FIG. 4A schematically shows a top view of the first stratum 210 of a nanopore. This first stratum 210 is a nanogap 111 in-between noble metal layers 115, 125. The first stratum 210 was fabricated with a sidewall technique by any of the fabrication embodiments presented already in the present disclosure. The nanogap 111 is cutting through the first stratum 210 separating the first stratum into the first layer 115 and the second layer 125. The first layer 115 contains a first noble metal and the second layer 125 contains a second noble metal. The first 115 and second 125 layers typically are composed of one or more noble metals. In a representative embodiment both layers are of Pd. As before, all the elements depicted in FIGS. 4A-4C that carry the same indicator numbers as elements in FIGS. 1A-1F are the indeed the same, and more of their properties need not to be repeated here.

FIG. 4B schematically shows a top view of the second stratum 220 of a nanopore. The second stratum 220 has a slit 121 cutting through it, separating the second stratum 220, into two side layers, a first side layer 215 and a second side layer 225. The materials making up the second stratum 220 are electrically insulating, typically dielectrics. The second stratum 220 typically has also been fabricated by a sidewall technique. The dimensions, or sizes, of the elements of the second stratum 220, such as the side layers 215 and 225, and the slit 121 typically may be close to those of the first stratum 210.

FIG. 4C schematically shows a top view of the a nanopore in which one of the strata is a nanogap in-between noble metals. The two strata are in direct contact with one another, with the noble metal stratum 210 shown on the top, by way of example. The nanogap 111 and the slit 121 in combination are forming a nanopore 250. In FIG. 4C the slit 121 and the nanogap 111 are crossing at a 90° angle, but other predetermined angles would be allowed, as well. Through the opened nanopore 250 two potential reservoirs on opposing sides of the nanopore structure would be in fluid connectivity, meaning molecules that would fit through the nanopore 250 would be able to pass. As in earlier discussed embodiments, the first 115 and the second 125 layers are provided with an electrical connection 175. Such connection then allows for a variety of electrical measurements in the nanopore framework, such as current measurements across the nanogap 111, as symbolically indicated in FIG. 4C. It is understood that the nanopore is part of, and is supported by, some device structure 150, as symbolically indicated in FIG. 4C. The embodiment of the disclosure presented with reference to FIGS. 4A-4C may be characterized as forming a nanopore with the capability of electrical measurements.

Figure 5:
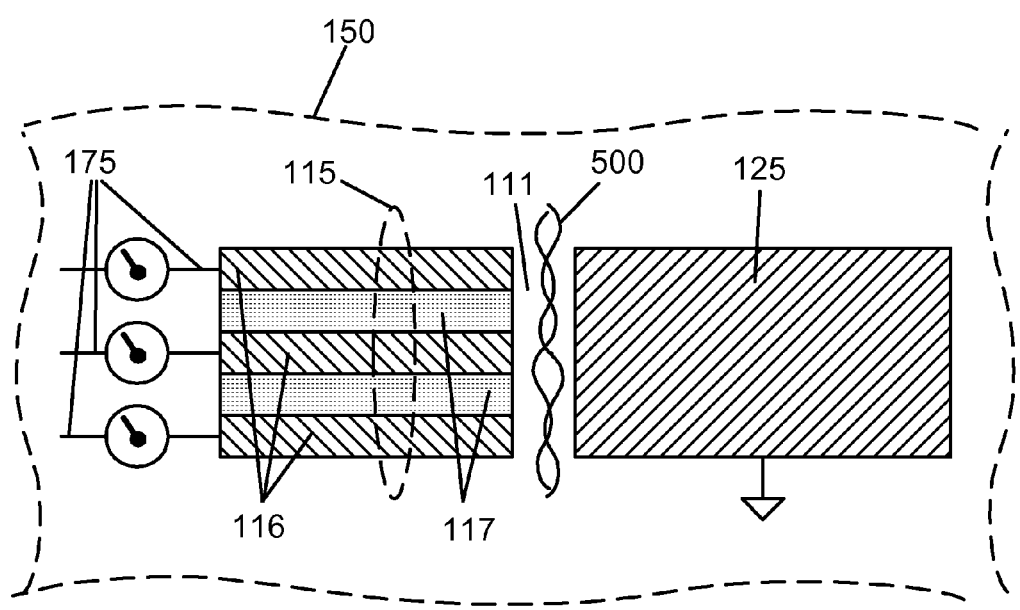
FIG. 5 schematically depicts a cross sectional view of a noble metal layer having sub-layer forming a side of a nanogap.

In all of the embodiments presented in this disclosure one may fabricate the nanogap in-between noble metals with sub-layers. FIG. 5 schematically depicts a cross sectional view of multilayered noble metals forming a side of a nanogap that is in-between noble metals. The two noble metal comprising layers 115, 125 are separated by the nanogap 111. By way of example, the first layer 115 is shown to contain sub-layers, but this should not be interpreted as a restriction, either of the two layers 115, 125, or both, could be made with a plurality of sub-layers. The sub-layers alternatively are either electrical insulators 117, such as dielectrics, or noble metal conductors 116. The advantage of such an arrangement is obvious since with electrical connections 175 to individual sub-layers one may carry out multiple simultaneous electrical investigations across the nanogap 111. The side opposite to the conductive noble metal sub-layers 116 in some embodiments may be attached to ground. By way of example, a strand of DNA 500 is symbolically shows passing through the nanogap 111, while possibly tunneling currents are simultaneously measured at several of its locations. It is understood that the nanogap that is in-between noble metals with sub-layers, just as with other embodiments, is supported by, and contained in, some device structure 150.

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention.

In addition, any specified material or any specified dimension of any structure described herein is by way of example only. Furthermore, as will be understood by those skilled in the art, the structures described herein may be made or used in the same way regardless of their position and orientation. Accordingly, it is to be understood that terms and phrases such as "under," "side," "over", "underneath", "parallel", "perpendicular", "vertical", etc., as used herein refer to relative location and orientation of various portions of the structures with respect to one another, and are not intended to suggest that any particular absolute orientation with respect to external objects is necessary or required.

The foregoing specification also describes processing steps. It is understood that the sequence of such steps may vary in different embodiments from the order that they were detailed in the foregoing specification. Consequently, the ordering of processing steps in the claims, unless specifically stated, for instance, by such adjectives as "before", "ensuing", "after", etc., does not imply or necessitate a fixed order of step sequence.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential feature, or element, of any or all the claims.

Many modifications and variations of the present invention are possible in light of the above teachings, and could be apparent for those skilled in the art. The scope of the invention is defined by the appended claims.

The invention claimed is:

1. A method, comprising:
   obtaining a structure comprising a first layer and an adjunct layer, the first layer and the adjunct layer having a common interface, the first layer and the adjunct layer being patterned to include exposed sidewalls;
   using a sidewall image transfer technique to form a sacrificial layer of a controlled thickness on the exposed sidewall of the first layer and on the exposed sidewall of the first adjunct layer, wherein said sacrificial layer is substantially perpendicular to said common interface;
   disposing a second layer covering said first adjunct layer, followed by disposing a second adjunct layer covering said second layer, wherein said sacrificial layer separates said sidewall of said first layer from a sidewall of said second layer;
   chemical-mechanical-polishing a first portion of said second adjunct layer until said second layer has an exposed portion over said first adjunct layer, a second portion of the second adjunct layer remaining in place over a portion of the second layer following the chemical-mechanical-polishing;

etching away said exposed portion of said second layer using an etch process selective relative to the first and second adjunct layers;

chemical-mechanical-polishing said first adjunct and said second adjunct layers until either of said first layer or said second layer become exposed;

etching away said sacrificial layer, thereby forming a nanogap of a selected width between the sidewall of the first layer and the sidewall of the second layer, the nanogap being essentially equal to the controlled thickness of the sacrificial layer;

wherein said first layer comprises a first noble metal and said second layer comprises a second noble metal.

2. The method of claim 1, wherein said method further comprises:

producing either said first layer or said second layer as a plurality of sub-layers, wherein said sub-layers alternatively are either electrical insulators or noble metal conductors.

3. The method of claim 1, wherein said first noble metal and said second noble metal are both Pd.

4. The method of claim 1, wherein said method further comprises:

providing an electrical connection to said first layer and to said second layer, enabling current measurements across said nanogap.

5. The method of claim 1, wherein said selected width of said nanogap is about between 0.5 nm and 100 nm, further including providing a substrate, the first layer being disposed over a first portion of the substrate, and wherein the step of disposing the second layer covering said first adjunct layer further includes disposing the second layer directly on a second portion of the substrate such that the sacrificial layer separates the sidewall of the first layer from the sidewall of the second layer.

6. The method of claim 5, wherein said selected width of said nanogap is about between 1.5 nm and 5 nm.

7. A method, comprising:

obtaining a first layer having an exposed sidewall, wherein said first layer comprises a first noble metal;

using sidewall image transfer to form a sacrificial layer of a controlled thickness only on said sidewall;

disposing a second layer covering said first layer and said sacrificial layer, wherein said second layer comprises a second noble metal;

chemical-mechanical-polishing (CMP) said second layer until said first layer is exposed; and etching away said sacrificial layer, thereby forming a nanogap having a selected width between the sidewall of the first layer and the second layer that essentially equals said controlled thickness.

8. The method of claim 7, wherein said method further comprises:

producing either said first layer or said second layer as a plurality of sub-layers, wherein said sub-layers alternatively are either electrical insulators or noble metal conductors.

9. The method of claim 7, wherein said chemical-mechanical-polishing of said second layer is carried out with a slurry comprising an abrasive substance, further wherein said chemical-mechanical-polishing further includes chemical-mechanical-polishing of said first layer whereby the first and second layers have essentially the same thickness following said chemical-mechanical-polishing.

10. The method of claim 7, wherein said first noble metal and said second noble metal are both Pd.

11. The method of claim 7, wherein said method further comprises:

providing an electrical connection to said first layer and to said second layer, enabling current measurements across said nanogap.

12. The method of claim 7, further including:

providing a substrate and a support layer on the substrate, the support layer including a trench extending therein, the first layer being positioned within a portion of the trench, wherein the step of disposing the second layer covering said first layer and said sacrificial layer further includes filling a further portion of the trench with the second layer.

13. The method of claim 7, wherein said selected width of said nanogap is about between 0.5 nm and 100 nm.

14. The method of claim 13, wherein said selected width of said nanogap is about between 1.5 nm and 5 nm.

15. A method, comprising:

fabricating a first stratum with a nanogap cutting through said first stratum separating said first stratum into a first layer and a second layer, wherein said first layer comprises a first noble metal and said second layer comprises a second noble metal, the fabrication of the first stratum comprising:

providing a substrate, the first layer being on a first portion of the substrate and including an exposed sidewall, using sidewall image transfer, forming a sacrificial layer having a controlled thickness on the exposed sidewall of the first layer, disposing the second layer over the first layer and a second portion of the substrate such that the sacrificial layer separates the sidewall of the first layer from a sidewall of the second layer, chemical-mechanical-polishing the second layer until said first layer is exposed, and etching away the sacrificial layer, thereby forming the nanogap having a selected width between the sidewalls of the first layer and the second layer that essentially equals the controlled thickness;

fabricating a second stratum with a slit cutting through said second stratum, and wherein said second stratum is electrically insulating;

positioning said first stratum and said second stratum in direct contact with each other such that said nanogap and said slit cross at a predetermined angle and form a nanopore extending through the first stratum and the second stratum, and providing an electrical connection to the first layer and the second layer enabling an electrical measurement across the nanogap.

16. The method of claim 15, wherein said method further comprises:

producing either said first layer or said second layer as a plurality of sub-layers, wherein said sub-layers alternatively are either electrical insulators or noble metal conductors.

17. The method of claim 15, wherein said first noble metal and said second noble metal are both Pd.

18. The method of claim 15, wherein said sacrificial layer is formed with the controlled thickness only on the sidewall of the first layer following sidewall image transfer.

19. The method of claim 15, wherein said nanogap is about between 0.5 nm and 100 nm wide.

20. The method of claim 19, wherein said nanogap is about between 1.5 nm and 5 nm wide.

* * * * *